(12) United States Patent
Rüther et al.

(10) Patent No.: US 6,405,872 B1
(45) Date of Patent: Jun. 18, 2002

(54) METHOD AND DEVICE OF IMPROVING THE SHELFLIFE OF TONOMETERED FLUIDS

(75) Inventors: Horst Rüther, Hart/Graz; Helmut List, Graz, both of (AT)

(73) Assignee: F. Hoffmann-La Roche AG, Basel (CH)

( * ) Notice: Subject to any disclaimer, the term of this patent is extended or adjusted under 35 U.S.C. 154(b) by 29 days.

(21) Appl. No.: 09/661,382

(22) Filed: Sep. 13, 2000

(30) Foreign Application Priority Data

Sep. 13, 1999 (AT) ............................................. 1570/99

(51) Int. Cl.⁷ ............................................... B65D 85/84
(52) U.S. Cl. ................... 206/524.1; 53/434; 206/484.2
(58) Field of Search ............................... 206/363, 438, 206/213.1, 524.1–524.4, 524.9, 484.2; 53/434, 449, 470; 436/11, 88; 604/403, 408, 409

(56) References Cited

U.S. PATENT DOCUMENTS

| 4,116,336 A |   | 9/1978 | Sorenson et al. |
| 4,266,941 A | * | 5/1981 | Sullivan ...................... 436/11 |
| 4,454,945 A | * | 6/1984 | Jabarin et al. ............ 206/524.3 |
| 4,872,553 A | * | 10/1989 | Suzuki et al. ............ 206/524.4 |
| 5,230,427 A | * | 7/1993 | Betts et al. ............... 206/213.1 |
| 5,257,986 A | * | 11/1993 | Herbert et al. ............... 604/403 |
| 5,780,302 A | * | 7/1998 | Conlon et al. ................. 436/11 |
| 6,315,767 B1 | * | 11/2001 | Dumont et al. ............. 604/403 |

FOREIGN PATENT DOCUMENTS

| EP | 0339491 | 11/1989 |
| EP | 0724152 | 7/1996 |
| WO | 8605590 | 9/1986 |
| WO | 9116238 | 10/1991 |
| WO | 9321533 | 10/1992 |
| WO | 9716309 | 5/1997 |

OTHER PUBLICATIONS

Abstract of JP 3–205533 to K. Shirakawa, entitled "Storage Container for Calibration . . . Method," Sep. 1991.

* cited by examiner

Primary Examiner—Luan K. Bui
(74) Attorney, Agent, or Firm—Dykema Gossett PLLC

(57) ABSTRACT

In order to improve the shelflife of tonometered fluids containing at least one dissolved gas component and being packaged in a flexible container, a gas phase containing at least the dissolved gas component of the fluid is additionally introduced into the flexible container. The volume of the tonometered fluid and the volume of the gas phase together amounting to less than the maximum filling volume of the flexible container, which is collapsed when it is empty but unfolding when it is being filled.

11 Claims, 3 Drawing Sheets

METHOD AND DEVICE OF IMPROVING THE SHELFLIFE OF TONOMETERED FLUIDS

BACKGROUND OF THE INVENTION

The invention relates to a method of improving the shelflife of tonometered fluids containing at least one dissolved gas component, and a container of flexible, gas-tight material which unfolds when it is being filled and collapses when it is being drained, preferably a multilayered aluminum laminate bag for receiving and storing tonometered fluid.

DESCRIPTION OF THE PRIOR ART

For the purpose of calibrating gas sensors it is possible to use the respective gases or tonometered fluids containing the respective gases in dissolved form. If other sensors (such as electrolyte sensors, pH sensors, substrate sensors, etc.) are to be calibrated in addition to the gas sensors in one and the same sensor assembly, and if the same conditions are to be established during calibration as for the analysis of liquid samples, the use of tonometered fluids is recommended.

These may be produced ad hoc by tonometry using precision gases from gas cylinders. This well-established practice has the disadvantage of requiring the use of separate gas cylinders which have to be exchanged at regular intervals and are subject to strict safety regulations.

As a suitable alternative pre-tonometered fluids could be used which are not hampered by the above restrictions. Problems may occur with storing the gassed fluids, above all, if the gas component does not enter a chemical bond but is only present in dissolved form.

It has been known for a long time to store such tonometered fluids in glass ampoules or metal cans, without any significant deviations in the originally set component concentrations during the shelflife of the fluid. Problems will occur during fluid withdrawal upon use in the devices to be calibrated, since the rigid containers require an air inlet for removal of the fluid. Due to the entry of air the gas phase above the fluid will change, leading to a change in the chemical composition of the fluid and the gases dissolved in it.

The situation described above may be improved by using flexible containers, such as plastic bags made from film material. In U.S. Pat. No. 4,116,336, for instance, a bag of flexible material is disclosed, which contains a reference solution for a blood gas analyzer. Avoiding a gas phase, the flexible, gas-tight bag contains a liquid exhibiting known values for pH, $PCO_2$ and $PO_2$ for a given temperature. The partial pressures of the gases are below 600 mmHg at 37° C. The reference solution according to U.S. Pat. No. 4,116,336 can contain non-soluble organic substances, such as fluorocarbons, in order to increase oxygen solubility and thus the total amount of oxygen. The flexible bag essentially consists of laminated film and is sealed at the seams.

In WO 97/16309 A1 another flexible bag is described, which contains an oxygen reference solution and is also made from laminated film. The inner layer of the film material, which is next to the reference solution, consists of a sealable polymer, the middle layer is an aluminum foil, and the outer layer is made from polyester. The shelflife of the calibrating solution is predicted to be 61 weeks at room temperature (25° C.), with a quoted deviation of 2 percent from the initial values. The change in gas values is a logarithmic function of exterior temperature, however. Thus, the shelflife will be reduced to about 1.3 weeks at 50° C., which may happen easily during transport (air transport, warehouses, etc.). A similar product, which is known as "Cal B" of Mallinckrodt Sensor Systems Inc, Ann Arbor, Mich., has a shelflife of only 7 weeks at 25° C.

Another flexible container is known from WO 93/21533 A1, which contains a calibrating medium with dissolved gases. Helium is used to stabilize the concentrations of the dissolved gases.

In EP 0 724 152 A2 a container is described, which is used for calibrating solutions and/or other fluids used in blood gas analysis. The container presented in one variant of the invention, which is made from flexible and gas-tight material, is provided with a self-sealing connecting element cooperating with a piercing element (hollow needle) of the analyzer.

WO 86/05590 A1 shows a device for the determination of blood parameters. Two tonometered reference solutions are used, for which flexible, gas-impermeable bags are provided, which do not include a gas headspace.

From JP 03-205 533 A2, finally, a device with two flexible bags is known. The entire system comprises an inner bag containing a calibrating solution, which is enclosed by a gas-tight outer bag filled with a gas phase. The inner bag has a defined permeability for $CO_2$ and $O_2$. Since the outer bag is filled with a gas phase the ambient pressure (outside of the bag system) provides no key for determination of the interior pressure of the fluid. Thus it is not possible to calculate the tonometric values. Other drawbacks concern production, as an inner bag and an outer bag must be manufactured, separately filled and separately sealed.

Flexible bags that are ready for calibration have yet another shortcoming as they will not be absolutely gas-tight. In addition, film oxidation may occur, which will also contribute to distorted $O_2$ values. When tonometered fluids are stored in the hitherto described flexible bags there will be the risk of micro bubbles which may form in the fluids if the bags are stored at a pressure below filling pressure (see for instance U.S. Pat. No. 4,116,336).

SUMMARY OF THE INVENTION

It is an object of this invention to propose a method of increasing the shelflife of tonometered fluids in flexible containers, and to further develop flexible containers for tonometered fluids such that the problem of the formation of micro bubbles can be mastered.

According to the invention this object is achieved by providing that a gas phase containing at least the dissolved gas component be additionally introduced into the flexible container, the volume of the tonometered fluid and the volume of the gas phase together amounting to less than the maximum filling volume of the flexible container.

Whereas known methods with flexible containers avoid a gas phase in order to permit the simple physical-chemical relationship between partial pressure, solubility, and concentration to be utilized for determination of the partial pressure, this idea is abandoned by the invention, and an additional gas phase is introduced into the flexible container, whose gas component is considerably higher than would be possible with the aqueous solution. As the flexible container will not be completely full, the foil from which the container is made will exert only a negligible force on the contents of the bag during each stage of filling or drainage, such that with a triple-layer laminate bag the pressure difference between interior and exterior pressure will amount to less than 1 mbar. As a consequence, the partial pressure of the gas or gases dissolved in the fluid can be determined by means of the exterior pressure (barometric pressure), which essentially corresponds to the interior pressure, and the temperature.

A container according to the invention, which is made from flexible, gas-tight material and contains a tonometered fluid with at least one dissolved gas component, is thus characterized in that the tonometered fluid occupies a first part of the volume, and that the flexible container holds a gas phase occupying a second part of the volume, which contains at least the gas component dissolved in the fluid, and that the first and second volume parts taken together amount to less than the maximum filling volume of the flexible container. The ratio of the volume parts of the tonometered fluid and the gas phase may be between 1:3 and 3:1, and preferably about 1:1.

If the storage concerns only dissolved tonometered gases, the gas volume compared to the liquid volume should be as large as possible to obtain good buffering. If chemically bonded gases, such as $CO_2$, are to be stored in their tonometered state in addition to dissolved gases, such as $O_2$, greater liquid volumes are required as a rule. It is thus necessary to calculate optimum volume ratios depending on the application concerned.

The plastic bags could be filled with accurately metered volumes of the respective gases and fluids, for example. In a simple variant of the invention it would also be possible, however, that the flexible container be inserted into a receptacle restricting the unfolding of the container to a predefined volume, and that a metered amount of the tonometered fluid be filled into the container, and that the gas phase be subsequently introduced, upon which the flexible container unfolds until the predefined volume is reached. Advantageously, the predefined volume amounts to 30–90%, preferably to 60–75% of the maximum filling volume.

BRIEF DESCRIPTION OF THE DRAWINGS

The invention will now be described in more detail with reference to the accompanying drawings, in which FIG. 1 side view of a flexible container in accordance with the invention.

DETAILED DESCRIPTION OF THE PREFERRED EMBODIMENT

Figure 1:
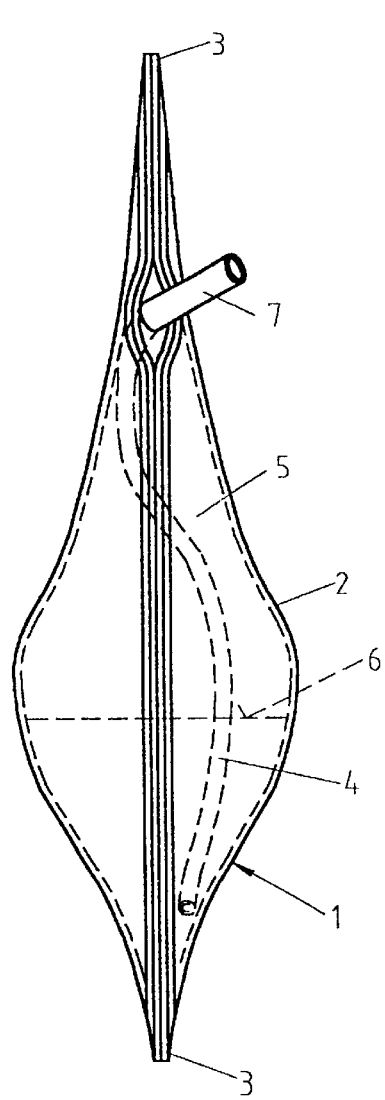
Figure 2:
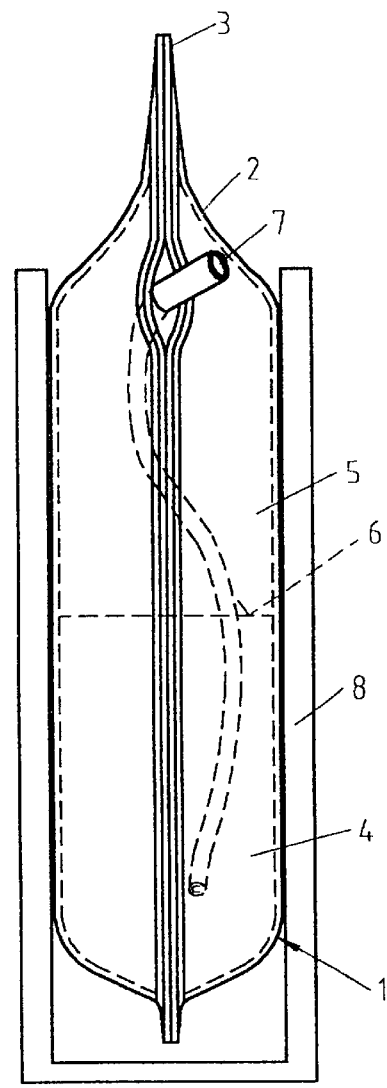
FIG. 2 is side view of the flexible container according to FIG. 1 held in a shaping frame.

The flexible container 1 presented in FIGS. 1 and 2 is made from a laminate film 2 sealed at the seams 3. The film material is multilayered and should be a high-grade laminate with respect to gas permeability. As has been found, however, even a commercially available simple aluminum laminate coated with a layer of polyethylene will give excellent storage stability.

A first part 4 of the volume is occupied by a tonometered fluid containing at least one dissolved gas component. The flexible container 1 further contains a gas phase occupying a second part 5 of the volume, which contains at least the gas component dissolved in the fluid. The liquid level separating the two volume parts 4 and 5 is referred to as 6. For the purpose of liquid withdrawal a tube 7 is provided in the bag, which tube is preferably made of polyethylene. It may be connected from each position along the sides of the bag. Preference is given to the position on top, in the area of the sealed seam 3, to prevent spilling of the fluid when the bag is opened and connected. The coupling should be gas-tight to ensure the stability of the reagents when inserted for use.

For filling the flexible container a receptacle 8, such as a shaping frame, may be used as is shown in FIG. 2, which will limit the unfolding of the container to a predefined volume. After removal of the shaping frame 8 the flexible bag exhibits the shape shown in FIG. 1, the volume defined by the frame amounting to 30–90%, and preferably 60–75% of the maximum filling volume. The tonometered fluid and the gas phase contain at least one gas component from the group of $O_2$, $CO_2$, $N_2$.

A tonometered fluid used in blood gas analysis, for instance, may have the following gas concentrations:

$cO_2=12\%$, $cCO_2=6\%$, $cN_2=82\%$

For the gas component $O_2$ with its critical shelflife this will imply that a filling volume of 200 ml aqueous solution at 25° C. without gas phase will exhibit only 0.62 ml oxygen in dissolved form according to the state of the art. If the 200 ml filling volume is made up of 100 ml aqueous solution and 100 ml gas volume, the oxygen volume will increase to 12.31 ml in this example, i.e. by a factor of about 20, which will explain the good storage properties.

Figure 3:
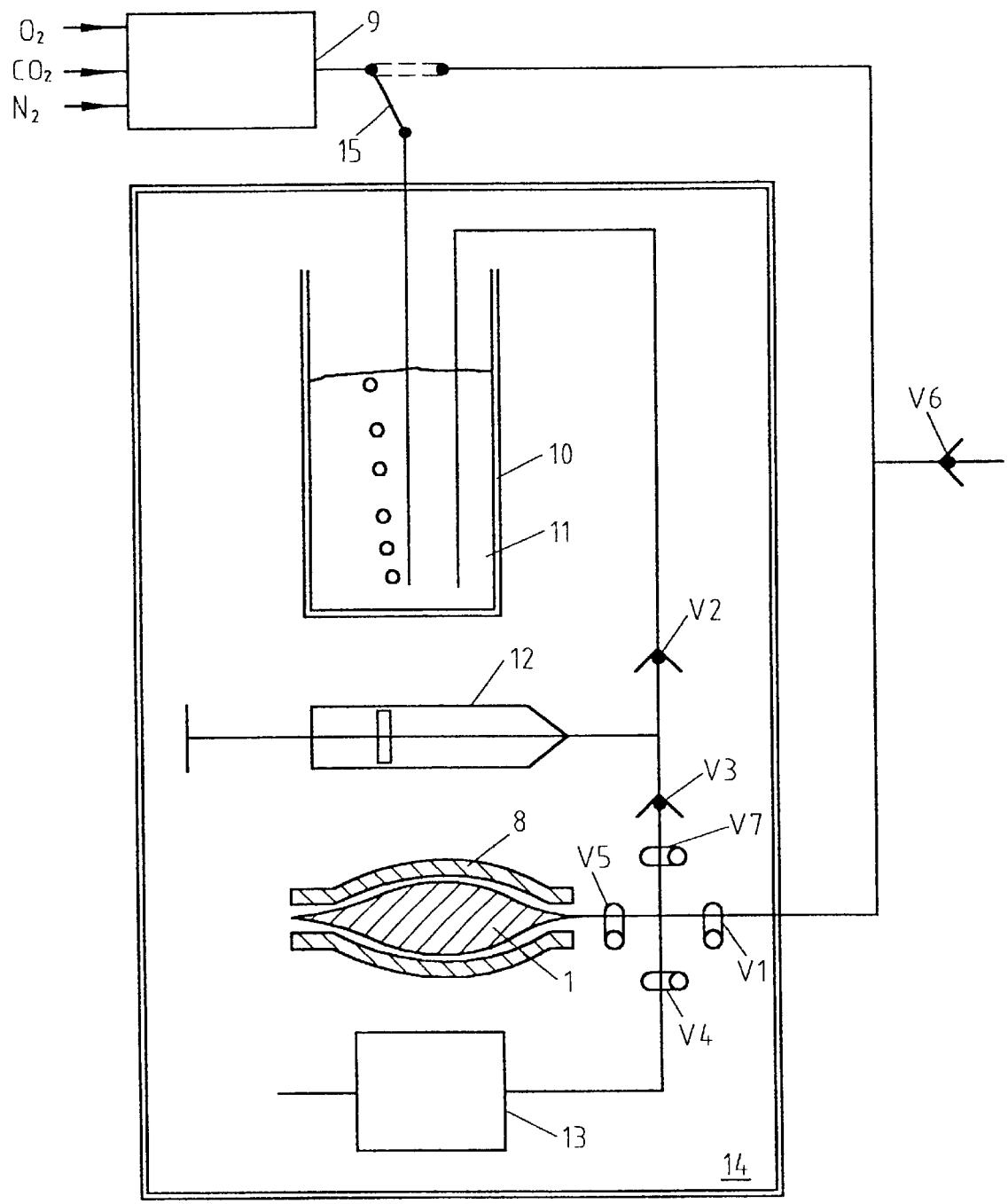
FIG. 3 shows a filling system for the flexible container.

FIG. 3 shows a possible filling system for the flexible container 1, which preferably comprises a high-precision gas mixer 9, a tonometering vessel 10 for the fluid 11 to be packaged, a metering device 12, a frame (or shaping receptacle) 8 for the flexible container 1, a vacuum pump 13, and a device 14 for temperature control of the individual components.

The filling process includes three steps:

$1^{st}$ step: Gas treatment of the flexible container to be filled, using a precision gas which is produced in the gas mixer 9 from the primary gases $O_2$, $CO_2$, $N_2$ and is advantageously used in the tonometering vessel 10 for tonometering the fluid 11 to be packaged.

In this step the two-way valve 15 is in the position marked by broken lines and the valves V1 and V5 are open, while valve V4 is closed. The pressure relief valve V6 will ensure that the flexible container 1 will not be damaged. The flexible container will then be evacuated via the vacuum pump 13, valve V1, V7 being closed and valves V4, V5 being open.

$2^{nd}$ step: Filling of the flexible container 1 by means of the metering device 12.

It has been found advantageous to couple the metering device 12 via two check valves V2 and V3, so that the metering device will draw a given amount of liquid from the tonometering vessel 10 via valve V2 and deliver it to the flexible container 1 via the check valve V3.

$3^{rd}$ step: Introducing of a defined volume of the precision gas.

After switchover of the two-way valve 15 into the position indicated by broken line the flexible container 1 is filled with precision gas until the flexible container presses against the wall of the shaping frame 8 and the pressure relief valve V6 opens.

After the filling process has been completed and the valve V5 has been closed the flexible container 1 may be removed from the receptacle 8 and the fitting of the bag may be closed.

Figure 4:
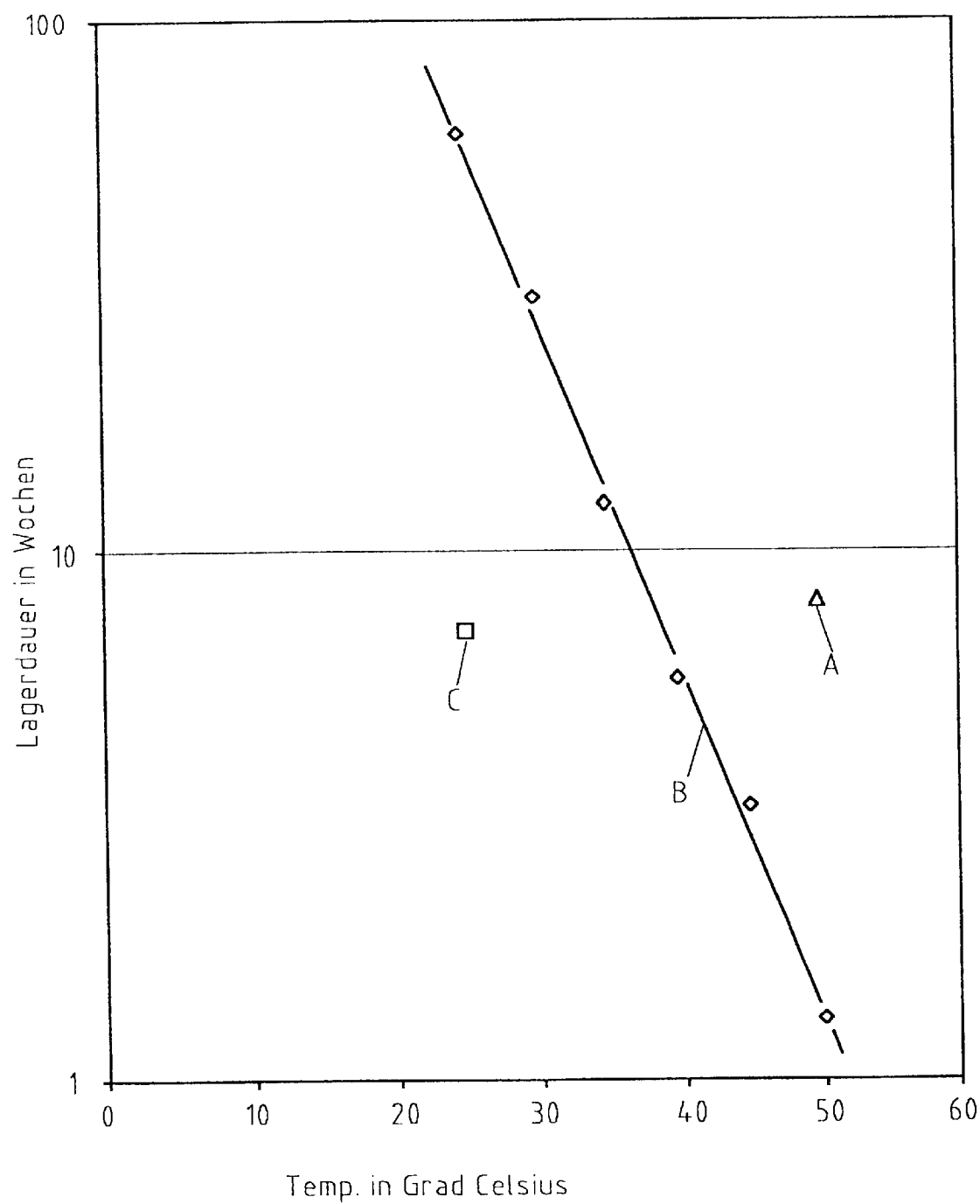
FIG. 4 is a diagram indicating the shelflife as a function of storage temperature.

FIG. 4 shows a diagram in which the shelflife (in weeks) is plotted against the temperature (in ° C.), with a tolerated deviation of 2% from the initial values. With the method of the invention it was possible to obtain a shelflife of 8 weeks for an electrolyte solution A with a bicarbonate buffer at a storage temperature of 50° C., with a deviation of 2% vis-a-vis the refrigerated storage of the electrolyte solution. Comparative values are provided by including graph B (information taken from WO97/16309) and point C (Mallinckrodt Sensor Systems Inc.), which refer to the limited shelflife of tonometered fluids obtained by previous methods.

We claim:

1. A method of improving the shelflife of a tonometered fluid containing at least one dissolved gas component and which is packaged in a flexible container that collapses when empty but unfolds when filled, comprising introducing a gas phase containing at least said dissolved gas component into said flexible container such that a combined volume of said tonometered fluid and said gas phase in said flexible container amounts to 90% or less of a maximum filling volume of said flexible container.

2. A method according to claim 1, wherein said flexible container is inserted into a receptacle restricting unfolding of said flexible container to a predefined volume, and wherein a metered amount of said tonometered fluid is filled into said container, and wherein said gas phase is subsequently introduced, upon which said flexible container unfolds until said predefined volume is reached.

3. A method according to claim 1, wherein said flexible container is a multilayered aluminum laminate bag.

4. A method according to claim 2, wherein said predefined volume amounts to 30–90% of said maximum filling volume.

5. A method according to claim 2, wherein said predefined volume amounts to 60–75% of said maximum filling volume.

6. A container containing a tonometered fluid with at least one gas component dissolved therein, which is made from flexible, gas-tight material and unfolds when it is being filled and collapses when it is being drained, wherein said tonometered fluid occupies a first volume part and wherein said flexible container holds a gas phase occupying a second volume part, said gas phase contains at least said gas component dissolved in said tonometered fluid, and wherein said first and second volume parts taken together amount to 90% or less of a maximum filling volume of said flexible container.

7. A container according to claim 6, wherein said tonometered fluid and said gas phase contain at least one gas component selected from the group consisting of $O_2$, $CO_2$ and $N_2$.

8. A container according to claim 6, wherein said flexible container is a multilayered aluminum laminate bag.

9. A container according to claim 6, wherein the ratio of said first and second volume parts of said tonometered fluid and said gas phase is between 1:3 and 3:1.

10. A container according to claim 6, wherein the ratio of said first and second volume parts of said tonometered fluid and said gas phase is about 1:1.

11. A method of improving the shelflife of a tonometered fluid containing at least one dissolved gas component and which is packaged in a flexible container that collapses when empty but unfolds when filled, comprising inserting said flexible container into a receptacle restricting unfolding of said flexible container to a predefined volume, filling a metered amount of said tonometered fluid into said flexible container, and introducing a gas phase containing at least said dissolved gas component into the flexible container so that said flexible container unfolds and so that a combined volume of said tonometered fluid and said gas phase in said flexible container amounts to 90% or less of a maximum filling volume of said flexible container.

* * * * *